United States Patent

Gough et al.

Patent Number: 5,925,042
Date of Patent: *Jul. 20, 1999

[54] MULTIPLE ANTENNA ABLATION APPARATUS AND METHOD

[75] Inventors: Edward J. Gough, Menlo Park; Alan A. Stein, Moss Beach, both of Calif.

[73] Assignee: Rita Medical Systems, Inc., Mt. View, Calif.

[*] Notice: This patent is subject to a terminal disclaimer.

[21] Appl. No.: 08/963,375

[22] Filed: Nov. 3, 1997

Related U.S. Application Data

[63] Continuation-in-part of application No. 08/585,532, Jan. 16, 1996, Pat. No. 5,672,174, which is a continuation-in-part of application No. 08/515,379, Aug. 15, 1995, Pat. No. 5,683,384.

[51] Int. Cl.⁶ .................................................. A61B 17/39
[52] U.S. Cl. ........................... 606/41; 606/49; 607/101; 607/102
[58] Field of Search ........................... 606/41, 42, 45–50; 607/100–102, 115, 116, 122, 156

[56] References Cited

U.S. PATENT DOCUMENTS

| | | |
|---|---|---|
| Re. 32,057 | 12/1985 | LeVeen . |
| Re. 32,066 | 1/1986 | LeVeen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | LeVeen . |
| 4,011,872 | 3/1977 | Komiya . |
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |
| 4,080,959 | 3/1978 | LeVeen . |
| 4,085,756 | 4/1978 | Weaver . |
| 4,095,602 | 6/1978 | LeVeen . |
| 4,119,102 | 10/1978 | LeVeen . |
| 4,121,592 | 10/1978 | Whalley . |
| 4,140,130 | 2/1979 | Storm, III . |
| 4,154,246 | 5/1979 | LeVeen . |
| 4,230,129 | 10/1980 | LeVeen . |
| 4,237,898 | 12/1980 | Whalley . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 566 450B1 | 10/1993 | European Pat. Off. . |
| 0 608 609 | 8/1994 | European Pat. Off. . |
| 2 283 701 | 4/1976 | France . |
| 2 670 664 | 6/1992 | France . |
| 10 07 960 | 10/1957 | Germany . |
| 21 24 684 | 11/1973 | Germany . |
| 89 09 492 U | 3/1990 | Germany . |
| 38 38 840 | 5/1990 | Germany . |
| 39 30 451 | 3/1991 | Germany . |
| 41 00 422 | 7/1992 | Germany . |

(List continued on next page.)

*Primary Examiner*—Michael Peffley
*Attorney, Agent, or Firm*—Wilson Sonsini Goodrich & Rosati

[57] ABSTRACT

An ablation treatment apparatus has a multiple antenna device. The multiple antenna device includes a primary antenna with a lumen, a longitudinal axis and an ablative surface area of length $L_1$. The multiple antenna device also includes a secondary antenna that is positionable in the primary antenna. A secondary antenna distal end is deployed at a selected tissue site from the primary antenna lumen in a lateral direction relative to the longitudinal axis. A sensor is at least partially positioned at an exterior of the secondary antenna distal end at a distance $L_2$ from the primary antenna along the secondary antenna distal end. $L_2$ is at least equal to ⅓ $L_1$. An energy source is coupled to the primary antenna.

41 Claims, 8 Drawing Sheets

U.S. PATENT DOCUMENTS

| | | |
|---|---|---|
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,892 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | Deluca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | LeVeen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Van't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | LeVeen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |
| 5,293,869 | 3/1994 | Edwards et al. . |
| 5,295,955 | 3/1994 | Rosen et al. . |
| 5,300,068 | 4/1994 | Rosar et al. . |
| 5,300,069 | 4/1994 | Hunsberger et al. . |
| 5,300,099 | 4/1994 | Rudie . |
| 5,304,214 | 4/1994 | Deford et al. . |
| 5,309,910 | 5/1994 | Edwards et al. . |
| 5,313,943 | 5/1994 | Houser et al. . |
| 5,314,466 | 5/1994 | Stern et al. . |

| | | | | | | |
|---|---|---|---|---|---|---|
| 5,322,503 | 6/1994 | Desai . | | 5,514,130 | 5/1996 | Baker . |
| 5,328,467 | 7/1994 | Edwards et al. . | | 5,514,131 | 5/1996 | Edwards . |
| 5,334,193 | 8/1994 | Nardella . | | 5,520,684 | 5/1996 | Imran . |
| 5,334,206 | 8/1994 | Daikuzono . | | 5,531,676 | 7/1996 | Edwards et al. . |
| 5,336,222 | 8/1994 | Durgin, Jr. et al. . | | 5,531,677 | 7/1996 | Lundquist et al. . |
| 5,342,357 | 8/1994 | Nardella . | | 5,536,240 | 7/1996 | Edwards et al. . |
| 5,348,554 | 9/1994 | Imran et al. . | | 5,536,267 | 7/1996 | Edwards et al. . |
| 5,354,296 | 10/1994 | Turkel . | | 5,540,655 | 7/1996 | Edwards et al. . |
| 5,363,861 | 11/1994 | Edwards et al. . | | 5,542,915 | 8/1996 | Edwards et al. . |
| 5,365,926 | 11/1994 | Desai . | | 5,542,916 | 8/1996 | Hirsch et al. . |
| 5,366,490 | 11/1994 | Edwards et al. . | | 5,542,928 | 8/1996 | Evans et al. . |
| 5,368,592 | 11/1994 | Stern et al. . | | 5,545,161 | 8/1996 | Imran . |
| 5,370,675 | 12/1994 | Edwards et al. . | | 5,545,171 | 8/1996 | Sharkey et al. . |
| 5,370,678 | 12/1994 | Edwards et al. . | | 5,545,193 | 8/1996 | Fleischman et al. . |
| 5,383,876 | 1/1995 | Nardella . | | 5,546,267 | 8/1996 | Frederiksen et al. . |
| 5,383,917 | 1/1995 | Desai et al. . | | 5,548,597 | 8/1996 | Edwards et al. . |
| 5,385,544 | 1/1995 | Edwards et al. . | | 5,549,108 | 8/1996 | Edwards et al. . |
| 5,397,339 | 3/1995 | Desai . | | 5,549,644 | 8/1996 | Lundquist et al. . |
| 5,398,683 | 3/1995 | Edwards et al. . | | 5,554,110 | 9/1996 | Edwards et al. . |
| 5,401,272 | 3/1995 | Perkins . | | 5,556,377 | 9/1996 | Rosen et al. . |
| 5,403,311 | 4/1995 | Abele et al. . | | 5,558,672 | 9/1996 | Edwards et al. . |
| 5,405,346 | 4/1995 | Grundy et al. . | | 5,558,673 | 9/1996 | Edwards et al. . |
| 5,409,453 | 4/1995 | Lundquist et al. . | | 5,560,358 | 10/1996 | Arnold et al. . |
| 5,411,025 | 5/1995 | Webster, Jr. . | | 5,562,703 | 10/1996 | Desai . |
| 5,417,687 | 5/1995 | Nardella . | | 5,599,345 | 2/1997 | Edwards et al. . |
| 5,421,819 | 6/1995 | Edwards et al. . | | 5,599,346 | 2/1997 | Edwards et al. . |
| 5,423,807 | 6/1995 | Milder . | | 5,609,151 | 3/1997 | Mulier et al. . |
| 5,423,808 | 6/1995 | Edwards et al. . | | 5,620,481 | 4/1997 | Desai et al. . |
| 5,423,811 | 6/1995 | Imran et al. . | | 5,817,092 | 10/1998 | Behl .......................................... 606/41 |
| 5,433,708 | 7/1995 | Nichols et al. . | | 5,827,276 | 10/1998 | LeVeen et al. ............................ 606/41 |
| 5,435,805 | 7/1995 | Edwards et al. . | | 5,855,576 | 1/1999 | LeVeen et al. ............................ 606/41 |
| 5,437,662 | 8/1995 | Nardella . | | | | |
| 5,437,664 | 8/1995 | Cohen et al. . | | | FOREIGN PATENT DOCUMENTS | |
| 5,456,662 | 10/1995 | Edwards et al. . | | | | |
| 5,456,682 | 10/1995 | Edwards et al. . | | 63-275632 | 11/1988 | Japan . |
| 5,458,596 | 10/1995 | Lax et al. . | | 2-121675 | 5/1990 | Japan . |
| 5,458,597 | 10/1995 | Edwards et al. . | | WO 92/10142 | 6/1992 | WIPO . |
| 5,462,521 | 10/1995 | Brucker et al. . | | WO 94/04220 | 3/1994 | WIPO . |
| 5,470,308 | 11/1995 | Edwards et al. . | | WO 94/10925 | 5/1994 | WIPO . |
| 5,470,309 | 11/1995 | Edwards et al. . | | WO 94/11059 | 5/1994 | WIPO . |
| 5,471,982 | 12/1995 | Edwards et al. . | | WO 94/17856 | 8/1994 | WIPO . |
| 5,472,441 | 12/1995 | Edwards et al. . | | WO 94/25110 | 11/1994 | WIPO . |
| 5,484,400 | 1/1996 | Edwards et al. . | | WO 94/26178 | 11/1994 | WIPO . |
| 5,486,161 | 1/1996 | Lax et al. . | | WO 95/19142 | 7/1995 | WIPO . |
| 5,500,012 | 3/1996 | Brucker et al. . | | WO 95/25471 | 9/1995 | WIPO . |
| 5,505,730 | 4/1996 | Edwards . | | WO 96/04860 | 2/1996 | WIPO . |
| 5,507,743 | 4/1996 | Edwards et al. . | | WO 96/29946 | 10/1996 | WIPO . |
| 5,509,419 | 4/1996 | Edwards et al. . | | WO 97/06739 | 2/1997 | WIPO . |

MULTIPLE ANTENNA ABLATION APPARATUS AND METHOD

REFERENCE TO RELATED APPLICATION

This application is a continuation-in-part of U.S. patent application Ser. No. 08/585,532; Filed: Jan. 16, 1996, now U.S. Pat. No. 5,672,174 which is a continuation-in-part of U.S. patent application Ser. No. 08/515,379, filed Aug. 15, 1995, now U.S. Pat. No. 5,683,384, both of which are incorporated herein by reference.

BACKGROUND OF THE INVENTION

1. Field of the Invention

This invention relates generally to an apparatus for the treatment and tissue masses, and more particularly, to an RF treatment apparatus suitable for multi-modality treatment that includes a primary antenna inserted into or adjacent to the selected mass, and one or more side deployed secondary antennas laterally deployed from the primary antenna.

2. Description of the Related Art

Current open procedures for treatment of tumors are extremely disruptive and cause a great deal of damage to healthy tissue. During the surgical procedure, the physician must exercise care in not cutting the tumor in a manner that created seeding of the tumor, resulting in metastasis. In recent years, development of products have been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed (i) changes in cell or nuclear membrane permeability or fluidity, (ii) cytoplasmic lysomal disintegration, causing release of digestive enzymes, (iii) protein thermal damage affecting cell respiration and the synthesis of DNA or PNA and (iv) potential excitation of immunologic systems. Treatment methods for applying heat to tumors include the use of direct contact radio-frequency (RE) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. No. 4,562,200; U.S. Pat. No. 4,411,266; U.S. Pat. No. 4,838,265; U.S. Pat. No. 5,403,311; U.S. Pat. No. 4,011,872; U.S. Pat. No. 5,385,544; and U.S. Pat. No. 5,385,544.

There is a need for a multiple antenna ablation apparatus that provides volumetric ablation of a selected tissue mass. There is a further need for a multiple antenna ablation apparatus with a primary antenna that has an electromagnetic energy delivery surface equal to $L_1$, a secondary antenna with a distal surface, and a sensor positioned a distance $L_2$ from the primary antenna along a distal surface of the secondary antenna.

SUMMARY OF THE INVENTION

Accordingly, an object of the invention is to provide a multiple antenna ablation apparatus which provides volumetric ablation of a selected tissue mass.

Another object of the invention is to provide a multiple antenna ablation apparatus which provides volumetric ablation of a selected tissue mass and includes a sensor positioned in the selected tissue mass.

Still another object of the invention is to provide a multiple antenna ablation apparatus with a primary antenna with an electromagnetic delivery surface length equal to $L_1$, a secondary antenna laterally deployed from the primary antenna, and a sensor positioned a distance $L_2$, from the primary antenna along a distal end surface of the secondary antenna.

These and other objectives are achieved in an ablation treatment apparatus with a multiple antenna device. The multiple antenna device includes a primary antenna with a lumen, a longitudinal axis and an ablative surface area of length $L_1$. The multiple antenna device also includes a secondary antenna that is positionable in the primary antenna. A secondary antenna distal end is deployed at a selected tissue site from the primary antenna lumen in a lateral direction relative to the longitudinal axis. A sensor is at least partially positioned at an exterior of the secondary antenna distal end at a distance $L_2$, from the primary antenna along the secondary antenna distal end. $L_2$ is at least equal to ⅓ $L_1$. An energy source is coupled to the primary antenna.

In another embodiment, a method for creating an ablation volume in a selected tissue mass provides an ablation device with a primary antenna with an electromagnetic energy delivery surface, a secondary antenna with a distal end, a sensor at least partially positioned at an exterior of the secondary antenna distal end, and an energy source coupled to the primary antenna. The primary antenna is inserted into the selected tissue mass. The secondary antenna is positioned in the primary antenna after the primary antenna is inserted into the selected tissue mass. The secondary antenna distal end is advanced out of the primary antenna lumen into the selected tissue mass in a lateral direction relative to a longitudinal axis of the primary antenna. Electromagnetic energy is delivered from the primary antenna ablation surface to the selected tissue mass. A temperature of the selected tissue mass is measured at the sensor. An ablation volume is created in the selected tissue mass.

In various embodiments, the length of $L_2$ is at least equal or greater than 50% of $L_1$, 75% or greater of $L_1$ at least equal to $L_1$ or is greater than $L_1$. Secondary antenna can be a passive electrode. The multiple antenna device can be operated in a monopolar or bipolar mode. Including a sensor on the surface of the secondary antenna distal end permits monitoring of the ablation and provides a measurement for volumetric ablation.

DETAILED DESCRIPTION

Figure 1:
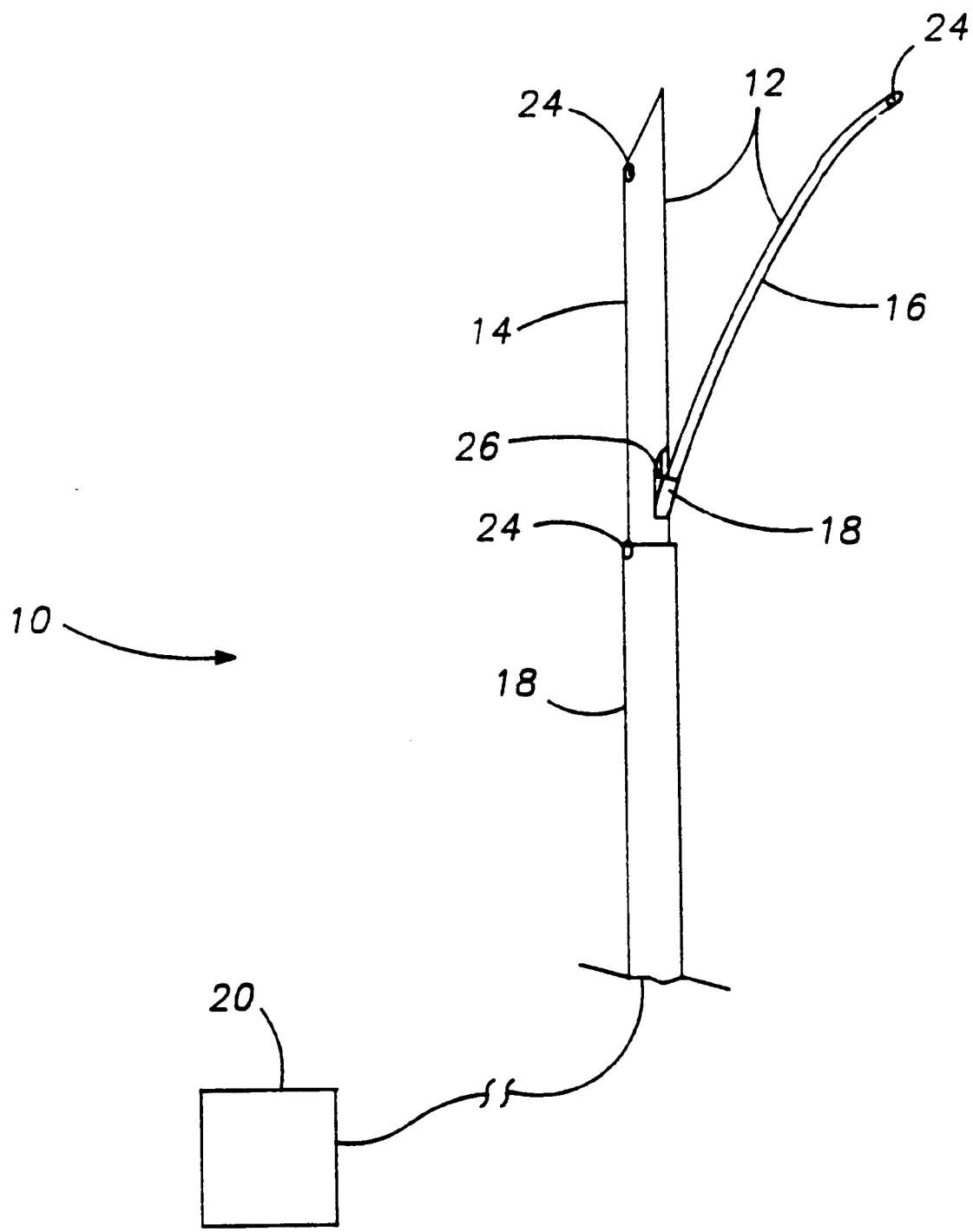
FIG. 1 is a perspective view of the multiple antenna ablation apparatus of the present invention illustrating a primary antenna and a single laterally deployed secondary antenna.

As shown in FIG. 1 an ablation treatment apparatus 10 includes a multiple antenna device 12. Multiple antenna device 12 includes a primary antenna 14, and one or more secondary antennas 16, which can be active or inactive electrodes. Secondary antennas 16 are inserted in a primary antenna lumen after primary antenna 14 has been advanced through tissue. When primary antenna 14 reaches a selected tissue ablation site in a selected tissue mass, including but not limited to a solid lesion, secondary antennas 16 are laterally deployed from the primary antenna lumen and into the selected tissue mass. Volumetric ablation proceeds from the interior of the selected tissue mass in a direction towards a periphery of the selected tissue mass.

In one embodiment each primary and secondary antenna 14 and 16 has an exterior ablation surface which delivers electromagnetic energy to the selected tissue mass. The length and size of each ablation surface can be variable. The length of primary antenna ablation surface relative to secondary antenna ablation surface can be 20% or greater, 33 and ⅓% or greater, 50% or greater, 75% or greater, about the same length, or greater than the length of secondary electrode ablation surface. Lengths of primary and secondary antennas 14 and 16 can be adjustable. Primary antenna 14 can be moved up and down, rotated about its Longitudinal axis, and moved back and forth, in order to define, along with sensors, the periphery or boundary of the selected tissue mass, including but not limited to a tumor. This provides a variety of different geometries, not always symmetrical, that can be ablated. The ablation can be between the ablation surfaces of primary and secondary antennas 14 and 16 when operated in a monopolar mode with a ground pad.

Primary antenna 14 is constructed so that it can be introduced percutaneously or laparoscopically through tissue without an introducer. Primary antenna 14 combines the function of an introducer and an electrode. Primary antenna 14 can have a sharpened distal end 14' to assist introduction through tissue. Each secondary antenna 16 has a distal end 16' that is constructed to be less structurally rigid than primary antenna 14. Distal end 16' is that section of secondary antenna 16 that is advanced from the lumen antenna 14 and into the selected tissue mass. Distal end is typically less structurally rigid that primary antenna 14. However, even though sections of secondary antenna 16 which are not advanced through the selected tissue mass may be less structurally rigid than primary antenna 14.

Structurally rigidity is determined by, (i) choosing different materials for antenna 14 and distal end 16' or some greater length of secondary antenna 16, (ii) using the same material but having less of it for secondary antenna 16 or distal end 16', e.g., secondary antenna 16 or distal end 16' is not as thick as primary electrode 14, or (iii) including another material in one of the antennas 14 or 16 to vary their structural rigidity. For purposes of this disclosure, structural rigidity is defined as the amount of deflection that an antenna has relative to its longitudinal axis. It will be appreciated that a given antenna will have different levels of rigidity depending on its length.

Primary and secondary antennas 14 and 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of primary or secondary antennas 14 or 16 can have different lengths. The lengths can be determined by the actual physical length of an antenna, the amount of an antenna that has an ablation delivery surface, and the length of an antenna that is not covered by an insulator. Suitable lengths include but are not limited to 17.5 cm, 25.0 cm. and 30.0 cm. The actual length of an antenna depends on the location of the selected tissue mass to be ablated. its distance from the skin, its accessibility as well as whether or not the physician chooses a laparoscopic, percutaneous or other procedure. Further ablation treatment apparatus 10, and more particularly multiple antenna device 12, can be introduced through a guide to the desired tissue mass site.

An insulation sleeve 18 may be positioned around an exterior of one or both of the primary and secondary antennas 14 and 16 respectively. Each insulation sleeve 18 can be adjustably positioned so that the length of an antenna ablation surface can be varied. Each insulation sleeve 18 surrounding a primary antenna 14 can include one or more apertures. This permits the introduction of a secondary antenna 16 through primary antenna 14 and insulation sleeve 18. This distance that a secondary antenna 16 extends from insulation sleeve defines the length of distal end 16'.

One or more sensors 24 may be positioned on interior or exterior surfaces of primary antenna 14, secondary antenna 16 or insulation sleeve 18. Preferably sensors 24 are positioned at primary antenna distal end 14', secondary antenna distal end 16' and insulation sleeve distal end 18'. Secondary antenna 16 can extend from insulation sleeve distal end 18' in a lateral direction relative to primary antenna 14, and sensor 24 can be positioned at insulation sleeve distal end 18'. Preferably, sensor 24 is positioned at least partially on an exterior surface of distal end 16'.

$L_1$ is the length of the electromagnetic energy delivery surface of primary antenna 14. $L_2$ is the distance from primary antenna 14 to sensor 24 when sensor 24 is positioned at least partially on an exterior of distal end 16'. $L_2$ is measured from primary antenna 14 along the surface of distal end 16'. In various embodiments, the length of $L_2$ is at least equal to or greater than 33.33% of $L_1$, 50% of $L_1$, 75% or greater of $L_1$, at least equal to $L_1$ or is greater than $L_1$. Sensors 24 permit accurate measurement of temperature at a tissue site in order to determine, (i) the extent of ablation, (ii) the amount of ablation (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, I type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at energy source 20 which then regulates the amount of energy delivered to primary and/or secondary antennas 14 and 16.

The geometry of the ablation is selectable and controllable. Any number of different ablation geometries can be achieved. This is more readily achievable with sensor 24 being positioned at or close enough to the periphery of the ablation.

In one embodiment, insulation sleeve I8 can comprise a polyamide material. Sensor 24 is at least partially positioned at an exterior of secondary antenna distal end I6'. A sensor 24 may be positioned on top of polyimide insulation sleeve 18. The polyamide insulation sleeve I8 is semi-rigid. Sensor 24 can lay down substantially along the entire length of polyamide insulation sleeve I 8. Primary antenna 14 is made of a stainless-steel hypodermic tubing with 2 cm of exposed ablation surface. Secondary antennas 16 have distal ends 16' that are made of NiTi hypodermic tubing. A handle may be included with markings to show the varying distance of secondary antennas 16 from primary antenna 14. Fluid infusion is delivered through a Luer port at a side of the handle. Type-T thermocouples are positioned at distal ends 16'.

An energy source 20 is connected to multiple antenna device 12 with one or more cables 22. Energy source 20 can be an RF source, microwave source, short wave source, laser source and the like. Multiple antenna device 12 can be comprised of primary and secondary antennas 14 and 16 that are RF electrodes, microwave antennas, as well as combinations thereof. Energy source 20 may be a combination PF/microwave box. Further a laser optical fiber, coupled to a lasersource 20 can be introduced through one or both of primary or secondary antennas 14 and 16. One or more of the primary or secondary antennas 14 and I6 can be an arm for the purposes of introducing the optical fiber.

Antennas 14 and 16 may be electromagnetically coupled by wiring, soldering, connection to a common couplet, and the like. This permits only one antenna 14 or 16 to be coupled to energy source 20 and use of a single cable 22.

Preferably, distal end 16' is laterally deployed relative to a longitudinal axis of primary antenna 14 out of an aperture 26 formed in primary antenna 14. Aperture 26 is at distal end 14' or formed in a side of an exterior of antenna 14.

A method for creating an ablation volume in a selected tissue mass includes inserting and advancing primary antenna 14 through tissue and into a selected tissue mass. Secondary antennas 16 are positioned in a lumen formed in antenna 14 while antenna 14 is advanced through tissue. At least one distal end 16' is deployed from the primary antenna lumen into the selected tissue mass in a lateral direction relative to the longitudinal axis of primary antenna 14. Electromagnetic energy is delivered from one of a primary antenna ablation surface. a secondary antenna ablation surface or both to the selected tissue mass. An ablation volume is created in the selected tissue mass. When operated in the monopolar mode. the ablation is between the ablation surfaces of the antennas.

There is wide variation in the amount of deflection of secondary antenna 16. For example, secondary antenna 16 can be deflected a few degrees from the longitudinal axis of primary antenna 14, or secondary antenna can be deflected in any number of geometric configurations, including but not limited to a "If" hook. Further, secondary antenna 16 is capable of being introduced from primary antenna 14 a few millimeters from primary antenna, or a much larger distance. Ablation by secondary antenna 16 can begin a few millimeters away from primary antenna 14, or secondary electrode 16 can be advanced a greater distance from primary antenna 14 and at that point the initial ablation by secondary antenna 16 begins.

Figure 2:
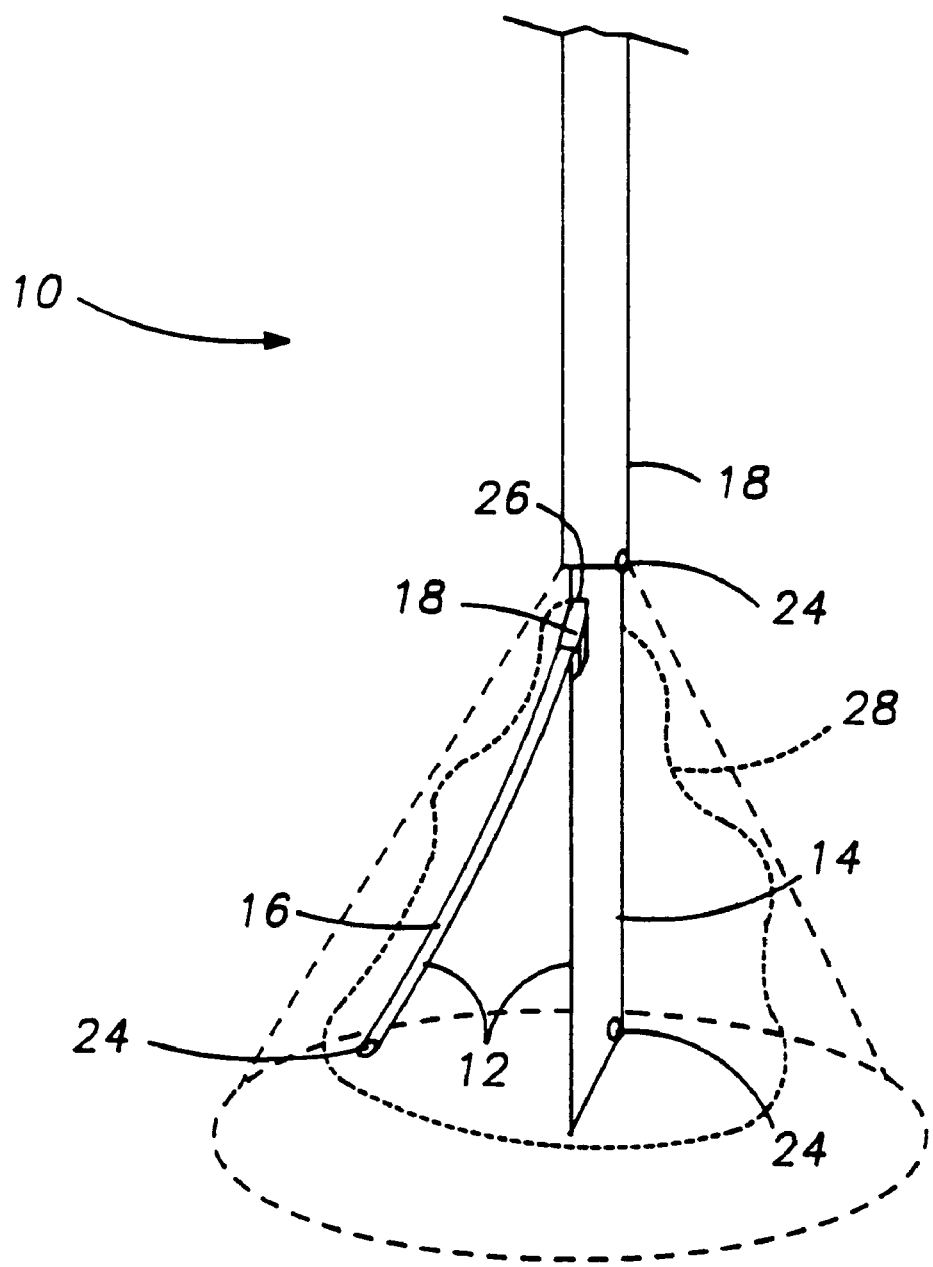
FIG. 2 is a perspective view of a conic geometric ablation achieved with the apparatus of FIG. 1.

As illustrated in FIG. 2, primary antenna 14 has been introduced into a selected tissue mass 28. Subsequently, secondary antenna distal end 16' is advanced out of aperture 26 and into selected tissue mass 28. Sensor 24 is positioned on distal end 16'. Insulation sleeves 18 can be included and may be fixed or adjusted. RF, microwave, short wave and the like energy is delivered to primary antenna 14, secondary antenna 16, or only to one. Either antenna 14 or 16 can be active or passive. In secondary antenna is active, then primary antenna distal end 14' includes a sensor 24. In this embodiment, $L_1$ is the length of the electromagnetic energy delivery surface of distal end 16', and $L_2$ is the distance from the tip of distal end 14' to the port positioned in primary antenna 14 from which secondary antenna 16 laterally extends. Antennas 14 and 16 can be operated in a monopolar mode (RF), or alternatively. multiple antenna device 12 can be operated in a bipolar mode (RF). Multi antenna device 12 can be switched between monopolar and bipolar operation and has multiplexing capability between antennas 14 and 16. Secondary antenna distal end 16' is retracted back into primary antenna 14, and primary antenna is then rotated. Secondary antenna distal end 16' is then introduced into selected tissue mass 28. Secondary antenna may be introduced a short distance into selected tissue mass 28 to ablate a small area. It can then be advanced further into any number of times to create more ablation zones. Again, secondary antenna distal end 16' is retracted back into primary antenna 14, and primary antenna 14 can be, (i) rotated again, (ii) moved along a longitudinal axis of selected tissue mass 28 to begin another series of ablations with secondary antenna distal end 16' being introduced and retracted in and out of primary antenna 14, or (iii) removed from selected tissue mass 28. A number of parameters permit ablation of selected tissue masses 28 of different sign and shapes including a series of ablations having primary and secondary antennas 14 and 16 with variable length ablation surfaces and the use of sensor 24. Again, primary 14 and secondary antenna 16 can be both active electrodes, or one may be an inactive electrode.

Figure 3:
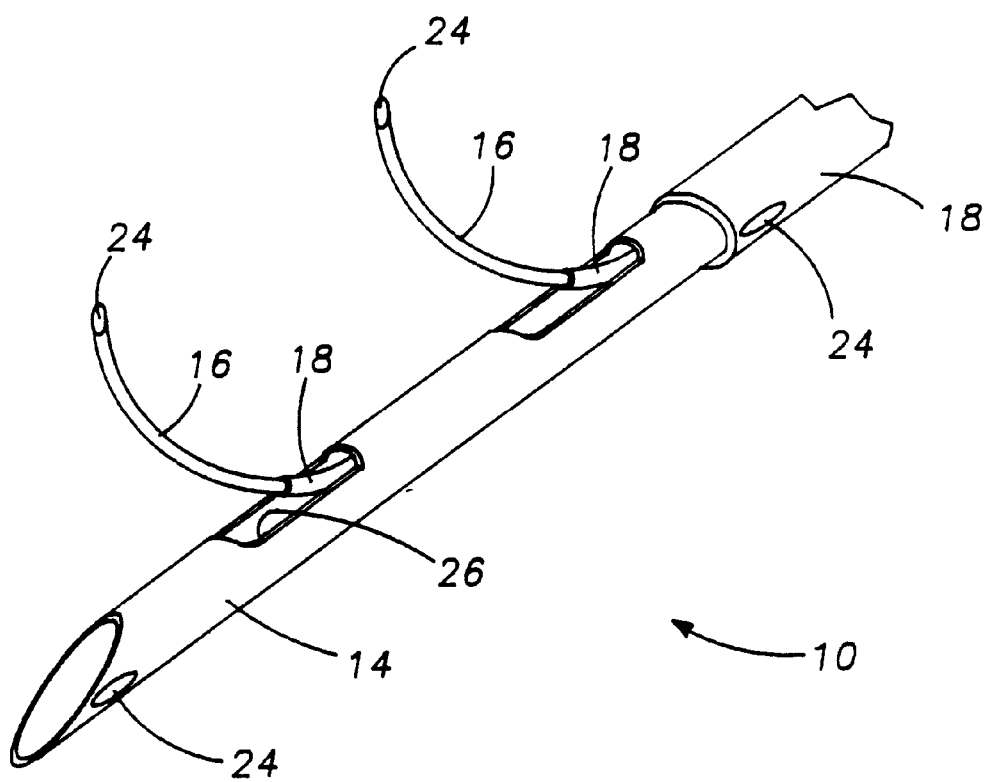
FIG. 3 is a perspective view of the multiple antenna ablation apparatus of the present invention with two secondary antennas deployed into the selected tissue mass.

In FIG. 3, two secondary antennas 16 are each deployed out of distal end 14' and introduced into selected tissue mass 28. Secondary antennas 16 form a plane and the area of ablation extends between the ablation surfaces of primary and secondary antennas 14 and 16. Primary antenna 14 can be introduced in an adjacent relation~o~ to selected tissue mass 28. This particular deployment is particularly useful for small selected tissue masses 28, or where piercing selected tissue mass 28 is not desirable. Primary antenna 14 can be rotated, with secondary antennas 16 retracted into a central lumen of primary antenna 14, and another ablation volume defined between the two secondary antennas 16 is created. Further, primary electrode 14 can be withdrawn from its initial position adjacent to selected tissue mass 28, repositioned to another position adjacent to selected tissue mass 28, and secondary antennas 16 deployed to begin another ablation cycle. Any variety of different positionings may be utilized to create a desired ablation geometry for selected tissue mass of different geometries and sizes.

Figure 4:
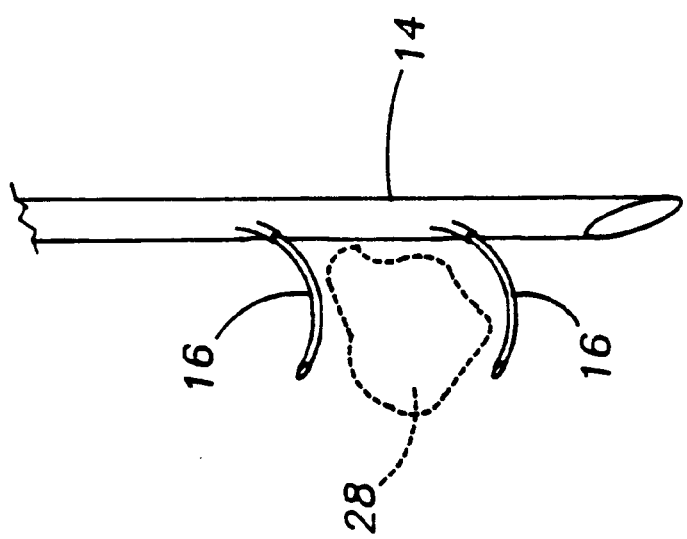
FIG. 4 is a perspective view illustrating the ablation created by the introduction of three secondary antennas into the selected tissue mass.

In FIG. 4 three secondary antennas 16 are introduced into selected tissue mass 28. The effect is the creation of an ablation volume without leaving non-ablated areas between antenna ablation surfaces. The ablation is complete.

Figure 5:
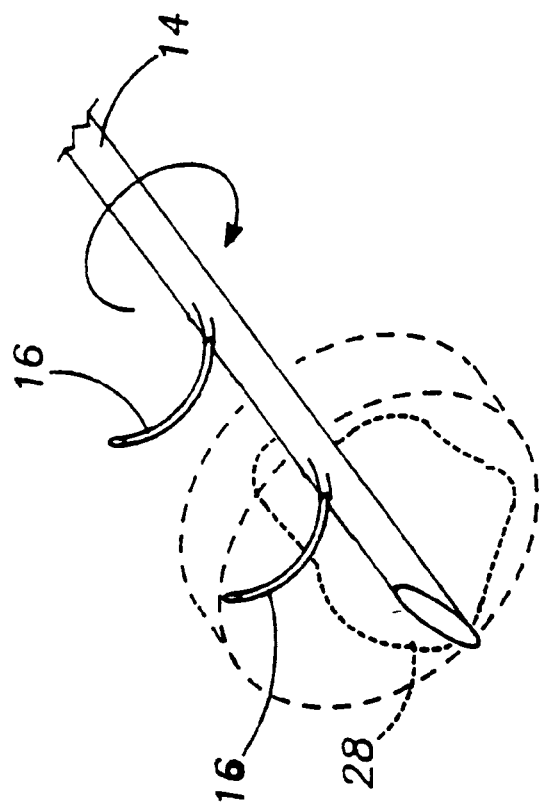
FIG. 5 is a perspective view illustrating the positioning of the multiple antenna ablation apparatus in the center of a selected tissue mass, and the creation of a cylindrical ablation.

Referring now to FIG. 5, a center of selected tissue mass 28 is pierced by primary antenna 14, secondary antennas 16 are laterally deployed and retracted, primary antenna 14 is rotated, secondary antennas 16 are deployed and retracted, and so on until a cylindrical ablation volume is achieved. Multiple antenna device 12 can be operated in the bipolar mode between the two secondary antennas 16, or between a secondary antenna 16 and primary antenna 14. Alternatively, multiple antenna device 12 can be operated in a monopolar mode.

Figure 6C:
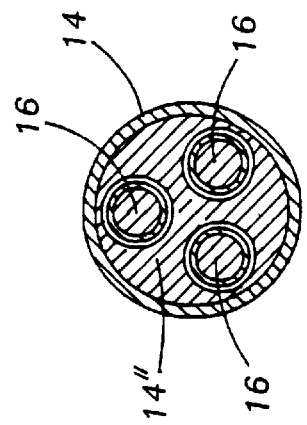
FIG. 6(c) is a cross-sectional view of the apparatus of FIG. 6(b) taken along the lines 6(c)—6(c).
Figure 6B:
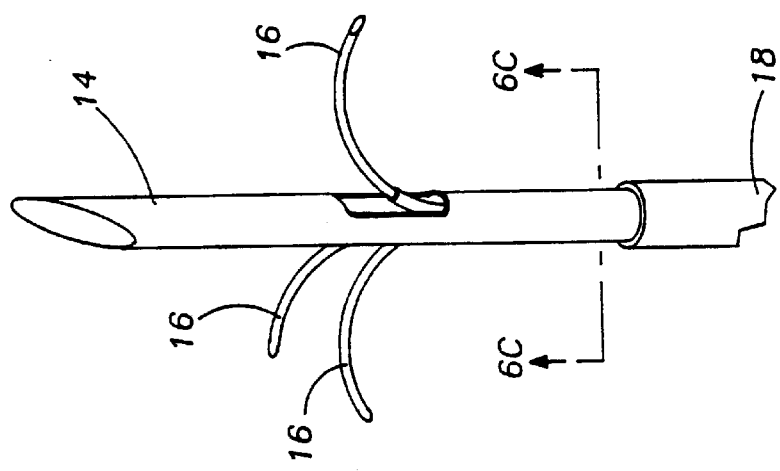
FIG. 6(b) is a perspective view of the multiple antenna ablation of the present invention illustrating three secondary antennas which provide a retaining and gripping function.
Figure 6A:
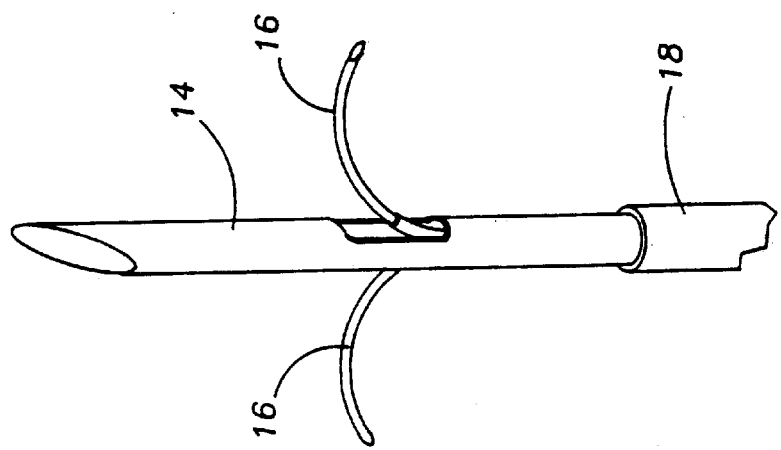
FIG. 6(a) is a perspective view of the multiple antenna ablation of the present invention illustrating two secondary antennas which provide a retaining and gripping function.

Secondary antennas 16 can serve the additional function of anchoring multiple antenna device 12 in a selected mass, as illustrated in FIGS. 6(a) and 6(b). In FIG. 6(a) one or both secondary antennas 16 are used to anchor and position primary antenna 14. Further, one or both secondary antennas 16 are also used to ablate tissue. In FIG. 6(b), three secondary antennas are deployed and anchor primary antenna 14.

FIG. 6(c) illustrates the infusion capability of multiple antenna device 12. Three secondary antennas 16 are positioned in a central lumen 14" of primary antenna 14. One or more of the secondary antennas 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums; contrast agents or dyes, and the like. An example of a therapeutic agent is a chemotherapeutic agent.

Figure 8:
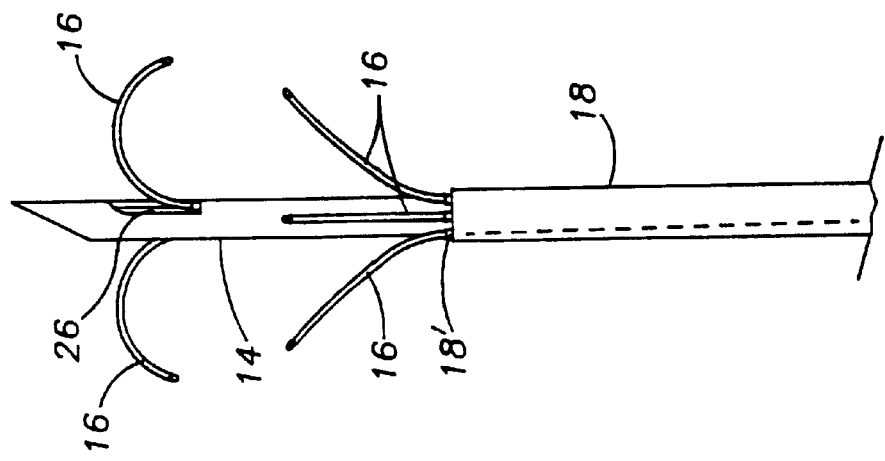
FIG. 8 is a perspective view of the multiple antenna ablation of the present invention illustrating the deployment of two secondary antennas from the primary antenna, and the deployment of three secondary antennas from the distal end of the insulation sleeve surrounding the primary antenna.
Figure 7:
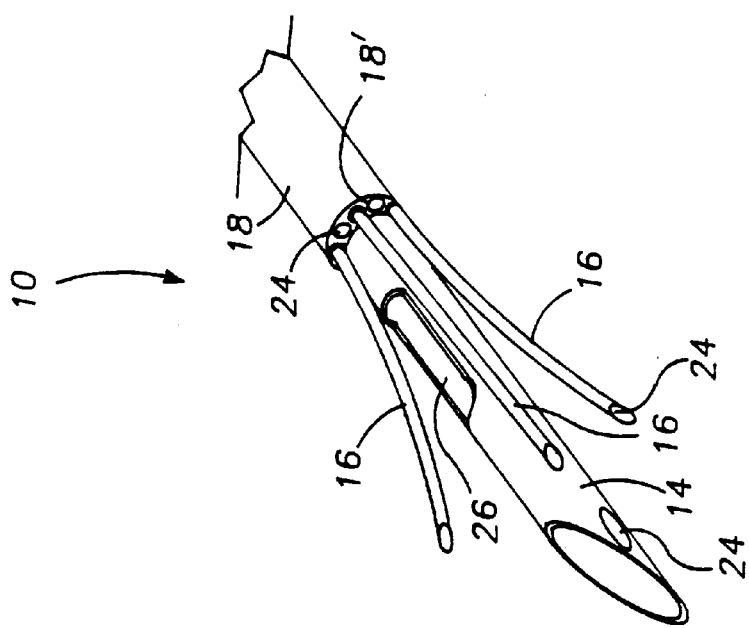
FIG. 7 is a perspective view of the multiple antenna ablation of the present invention illustrating the deployment of three secondary antennas from a distal end of the insulation sleeve surrounding the primary antenna.

As shown in FIG. 7 insulation sleeve 18 can include one or more lumens for receiving secondary antennas 16 which are deployed out of an insulation sleeve distal end 18'. FIG. 8 illustrates three secondary antennas 16 being introduced out of insulation sleeve distal end 18', and two secondary antennas 16 introduced through apertures 26 formed in primary antenna 14. As illustrated, the secondary electrodes introduced through apertures 26 provide an anchoring function. It will be appreciated that FIG. 8 shows that secondary antennas 16 can have a variety of different geometric configurations in multiple antenna device 12.

Resources, which can be hardware, software, or a combination of both, are connected with sensors 24, primary and secondary antennas 14 and 16 and energy source 20 to provide an output for delivering and maintaining a selected energy at primary and secondary antennas 14 and 16, e.g., feedback control. Further, the resources provide an output that maintains a selected energy at primary and secondary antennas for a selected length of time.

The following discussion pertains particularly to the use of an RF energy source and RF multiple antenna device 12. It will be appreciated that devices similar to those associated with RF multiple antenna device 12 can be utilized with laser optical fibers, microwave devices and the like.

Figure 9:
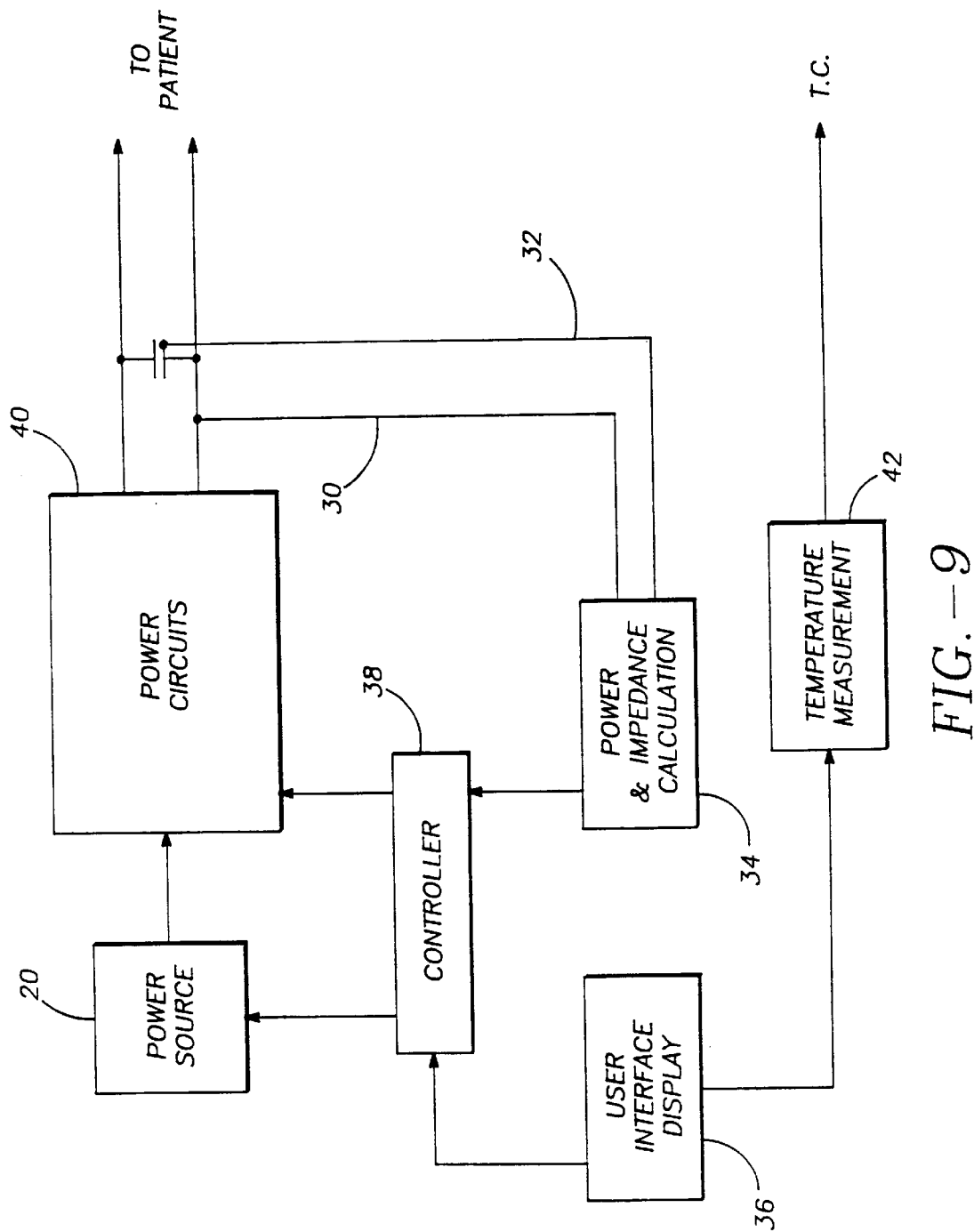
FIG. 9 is a block diagram illustrating the inclusion of a controller, energy source and other electronic components of the present invention.
Figure 10:
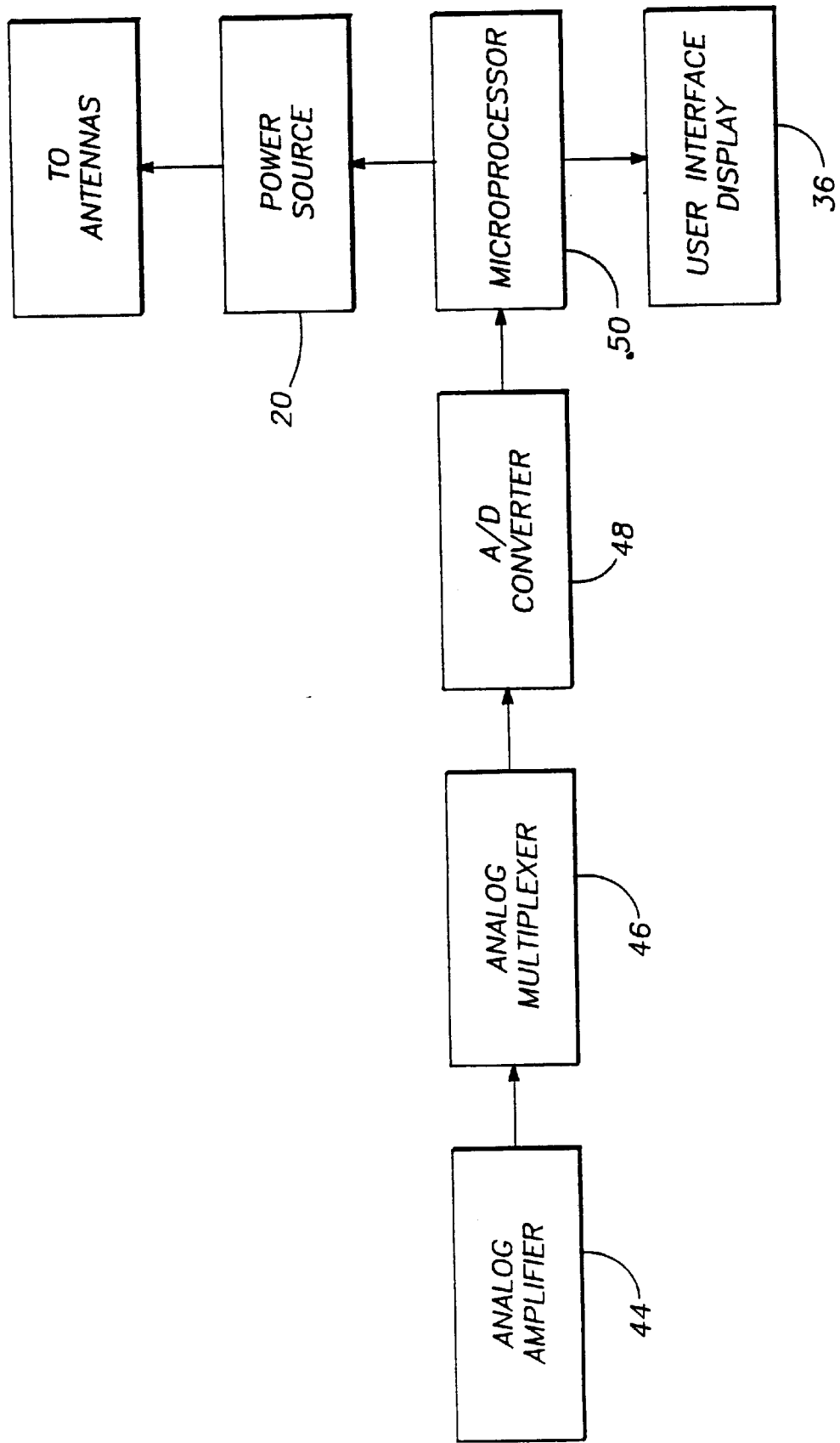
FIG. 10 is a block diagram illustrating an analog amplifier; analog multiplexer and microprocessor used with the present invention.

Referring now to FIG. 9 current delivered through primary and secondary antennas 14 and 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at the respective primary and/or secondary antennas 14 and 16.

In a similar manner, temperatures detected at sensors 24 provide feedback for maintaining a selected power. The actual temperatures are measured at temperature measurement device 42. and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered between primary antenna 14 and secondary antennas 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at primary and secondary antennas 14 and 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power that is independent of changes in voltage or current, and are used to change, (i) the selected power, including RF. microwave. laser and the like. (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Referring now to FIG. 9, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50.

Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced modified or interrupted. A control signal from microprocessor 50 can modify the power level supplied by power source 36. The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation treatment apparatus, comprising:
   a multiple antenna device including a primary antenna with a lumen, a longitudinal axis and an ablative surface area of length $L_1$, and a secondary antenna positionable in the primary antenna and including a secondary antenna distal end deployable at a selected tissue site from the primary antenna lumen in a lateral direction relative to the longitudinal axis;
   a sensor at least partially positioned at an exterior of the secondary antenna distal end at a distance $L_2$ from the primary antenna along the secondary antenna distal end, wherein $L_2$ is at least equal to $\frac{1}{3} L_1$; and an energy source coupled to the primary antenna.

2. The apparatus of claim 1, wherein $L_2$ is at least equal to $\frac{1}{2} L_1$.

3. The apparatus of claim 1, wherein $L_2$ is at least equal to $L_1$.

4. The apparatus of claim 1, further comprising:
   a sensor monitoring device coupled to the sensor.

5. The apparatus of claim 4, wherein the sensor monitoring device is a temperature monitoring device.

6. The apparatus of claim 1, further comprising:
   a feedback control device coupled to the energy source and the sensor, wherein the feedback control device is responsive to a detected characteristic from the sensor and provides a delivery of electromagnetic energy output from the energy source the primary antenna.

7. The apparatus of claim 1, wherein the secondary antenna is an inactive electrode and the primary antenna is an active electrode.

8. The apparatus of claim 1, wherein the secondary antenna distal end is structurally less rigid than the primary antenna.

9. The apparatus of claim 1, wherein the apparatus is switchable between bipolar and monopolar operation.

10. The apparatus of claim 1, wherein the primary antenna is hollow and coupled to an infusion medium source to receive an infusion medium.

11. The apparatus of claim 1, wherein the primary antenna has an ablation surface with a length that is at least 20% of a length of an ablation surface of the secondary antenna.

12. The apparatus of claim 1, the primary antenna has an ablation surface with a length that is at least one-third of a length of an ablation surface of the secondary antenna.

13. The apparatus of claim 1, wherein the primary antenna has an ablation surface with a length that is at least one-half of a length of an ablation surface of the secondary antenna.

14. The apparatus of claim 1, wherein two secondary electrodes are provided and laterally deployed from the primary antenna, each of the primary and secondary antennas having an ablation surface to create an ablation volume between the ablation surfaces.

15. The apparatus of claim 1 wherein three secondary electrodes are provided and laterally deployed from the primary antenna, each of the primary and secondary antennas having an ablation surface to create an ablation volume between the ablation surfaces.

16. The apparatus of claim 1, further comprising:
   an insulation sleeve positioned in a surrounding relationship around at least a portion of an exterior of the primary antenna.

17. The apparatus of claim 16, wherein the insulation sleeve is adjustably moveable along an exterior of the primary antenna.

18. The apparatus of claim 1, further comprising:

an insulation sleeve positioned in a surrounding relationship around at least a portion of an exterior of the secondary antenna.

19. The apparatus of claim 18, wherein the insulation sleeve is adjustably moveable along an exterior of the secondary antenna.

20. The apparatus of claim 1, further including a ground pad electrode with the primary antenna operating in a monopolar mode.

21. The apparatus of claim 1, wherein the primary antenna is an RF antenna.

22. The apparatus of claim 1, wherein the primary antenna is a microwave antenna.

23. The apparatus of claim 1, wherein the secondary antenna is an inactive antenna.

24. The apparatus of claim 1, wherein the primary antenna is hollow and coupled to an infusion medium source to receive an infusion medium.

25. The apparatus of claim 1, wherein the secondary antenna distal end is less structurally rigid than the primary antenna.

26. The apparatus of claim 1, further comprising: a cooling element coupled to the primary antenna.

27. The apparatus of claim 26, wherein the cooling element comprises:

a structure positioned in an interior of the primary antenna including at least one channel configured to receive a cooling medium.

28. The apparatus of claim 27, wherein the cooling medium is recirculated through the channel.

29. The apparatus of claim 27, wherein the distal end of the primary antenna is open.

30. The apparatus of claim 27, wherein the distal end of the primary antenna is closed.

31. The apparatus of claim 27, wherein the cooling element is positioned in an interior of the primary antenna.

32. The apparatus of claim 27, wherein the cooling element is positioned at an exterior surface of the primary antenna.

33. The apparatus of claim 27, wherein the cooling element is positioned within a wall defining the primary antenna.

34. A method for creating an ablation volume in a selected tissue mass, comprising:

providing an ablation device with a primary antenna with an electromagnetic energy delivery surface, a secondary antenna with a distal end, a sensor at least partially positioned at an exterior of the secondary antenna distal end, and an energy source coupled to the primary antenna;

inserting the primary antenna into the selected tissue mass;

inserting the secondary antenna at least partially in the primary antenna after the primary antenna is advanced through the selected tissue mass;

advancing the secondary antenna distal end out of the primary antenna lumen and into the selected tissue mass in a lateral direction relative to a longitudinal axis of the primary antenna;

delivering electromagnetic energy from the primary antenna ablation surface to the selected tissue mass;

measuring a temperature of the selected tissue mass at the sensor; and creating an ablation volume in the selected tissue mass.

35. The method of claim 34 wherein the secondary antenna is a inactive antenna.

36. The method of claim 34, wherein the secondary antenna distal end is an electromagnetic energy delivery surface.

37. The method of claim 36, wherein secondary antenna distal end is advanced out of a distal end of the primary antenna.

38. The method of claim 34, wherein the ablation device is operated in a monopolar mode.

39. The method of claim 34, wherein the ablation device is operated in a bipolar mode.

40. The method of claim 34, wherein the ablation device is switchable between monopolar and bipolar operation.

41. The method of claim 34, wherein the sensor measures temperature.

* * * * *